United States Patent [19]

Frome

[11] Patent Number: 5,571,794
[45] Date of Patent: Nov. 5, 1996

[54] NON-INVASIVE NOVEL METHOD FO COSMETIC LIP AUGMENTATION

[76] Inventor: Bruce M. Frome, 415 N. Crescent Dr., #220, Beverly Hills, Calif. 90210

[21] Appl. No.: 493,675

[22] Filed: Jun. 22, 1995

[51] Int. Cl.$^6$ .................... A61K 31/70; A61K 31/395; A61K 31/44; A61K 31/22; A61K 31/16; A61K 31/12; A61K 31/075; A61K 31/05

[52] U.S. Cl. .............. 514/23; 514/210; 514/356; 514/550; 514/627; 514/678; 514/720; 514/734; 514/844; 514/929

[58] Field of Search ................ 514/23, 210, 356, 514/550, 627, 678, 720, 734, 844, 929

[56] References Cited

PUBLICATIONS

Gomez, J. Lip Augmentation (letter), Plastic Reconstruction Surgery 1993 pp. 765–766.
Samiian, M. R. Lip Augmentation for correction of thin lips, Plastic Reconstruction Surgery 1993 pp. 162–166.
Matti, B. A., Nicolle, F. A. Clinical use of Zyplast collogen, Athesetic Plastic Surgery 1990 pp. 227–234.
Linder, R. M. Asthetic enhancement of the lips/grafts, Plastic Reconstruction Surgery 1992 pp. 1083–1090; 1091–1092.
Lassus, C., Surgical vermillion augmentation, Aesthetic Plastic Surgery 1992 pp. 123–127.
Karita, K., Izumi H., Pathways of vasodilator reflex, J. Auton Nerve System 1993 pp. 235–240.
Elson, M. L., Clinical asssessment of Zyplast Implant, J. American Acadamy Dermatology 1988 pp. 707–713.
Gonzales, Ulloa M., The sensuous lip,/Zyplast, Aesthetic Plastic Surgery 1992 pp. 231–236.

*Primary Examiner*—Kimberly Jordan

[57] ABSTRACT

A cosmetic treatment for inducing upper and lower lip augmentation in humans, wherein an active ingredient encouraging vasodilatation, preferably an ultra highly diluted homeopathic, ultra highly diluted element, local irritant or direct local vasodilator or a combination of two or more is administered by topical application or sublingually or gum by chewing. The vasodilators singly or in combinations of preferably ultra highly diluted elements, homeopathics, local irritant or vasodilators are diluted to preferably ten to fifteen percent for topical administration in a cosmetic cream or cosmetic gel or oral sublingual drops diluted in a 2% alcohol base or a five percent fructose-coated chewing gum. The treatment results in a significant non-invasive augmentation of both the upper and lower lip that onsets within a few moments and is effective for a duration on an average of four and one half hours.

12 Claims, No Drawings

NON-INVASIVE NOVEL METHOD FO COSMETIC LIP AUGMENTATION

BACKGROUND—FIELD OF THE INVENTION

This invention relates to the field of cosmetics and more particularly to the field of lip enlargement by the use of topically applied agents.

BACKGROUND—DISCUSSION OF PRIOR ART

Thin lips, especially in women, are generally considered unattractive. A variety of surgical, implant and injection techniques have been utilized to improve the appearance of women with thinner appearing lips. More recently, these techniques have been offered for women with lips of even "normal" size as the "bee sting" look came into vogue. These techniques include plastic surgical procedures implanting fat or lifting flaps in a similar manner to those used in cleft palate or hare lip repair; injections of collagen every two to three months or tattooing larger lips over smaller, thinner ones. Each of these procedures has obvious disadvantages.

Surgical procedures are costly, sometimes amounting to over ten thousand dollars by the time the plastic surgeon, anesthesiologist and operating room are paid for. Once the surgery is performed, the result is irreversible. If the appearance turns out to be unappealing, the person with the "new lips" is stuck with it. Aesthetic lip surgery is no less subject to all the common surgical complications than any other surgery, including infection and death from anesthesia and other consequences.

Collagen injections of the lips are expensive, costing hundreds of dollars. They must be frequently repeated as the body "dissolves" the collagen, requiring repeated injections if one is going to maintain that "full lips" appearance.

The biggest problem with collagen appears to be allergy to a foreign substance. A large percentage of women cannot accept collagen as their body rejects it by causing an antigen antibody response and sometimes a severe allergic reaction. These allergies to collagen have frequently progressed to auto immune reactions with sequelae similar to those suffered by recipients of silicone breast implants.

Tattooing of the lips has all the disadvantages of both surgery and collagen injections in that the result is irreversible, the procedure is expensive and painful and is fraught with complications of all invasive procedures such as infection and allergies.

SUMMARY OF THE INVENTION

The invention provides a method of utilizing the topical application of various active ingredients in a gel or lipstick base, or in a gum, or in sublingual drops or spray to achieve an enlargement of both the upper and lower lips.

The method utilizes active ingredients that are a combination of ultra high dilutions of natural substances or mineral elements or of other compounds or of peripheral vasodilators or irritants to achieve the augmented appearance of the lips as well as result in an actual increase in the size of the lips.

Each group of active ingredients is believed to have different mechanisms of action but each group achieves a measurable and observable increase in the size of the lips.

This invention has many advantages over existing methods of lip augmentation and is relatively inexpensive, reversible, painless and safe as opposed to the methods currently used to achieve a pleasing, full lip appearance.

SELECTION OF STUDY PARTICIPANTS

Twenty women, ages 14–69, with at least one thin appearing lip were selected on a consecutive basis. Four men, ages 18 to 56, were also selected who demonstrated the appearance of at least one thin lip.

There were three observers, two female and one male (one of whom was also an experienced plastic surgeon who had performed lip augmentation and was experienced in lip measurements). All three observers plus the study participant had to agree that the study participant had at least one thin appearing lip that if augmented would enhance his or her appearance.

OBJECTIVES OF THE STUDY

1) To determine if ultra highly diluted elements when applied topically to the lips will result in an augmentation of the lip size.

2) To determine if a vasodilator when applied topically to the lips will result in an augmentation of the lip size.

3) To determine if a topical local skin irritant when applied to the lips will result in an augmentation of the lip size.

4) To determine which topically applied substance, if any, resulted in the greatest augmentation of the lip.

5) To determine the duration of action as well as time of onset, if any, of the lip augmentation.

6) To determine, in all cases, if there occurred or did not occur a statistically significant measurable increase in lip size and/or only a significant appearance of lip augmentation unrelated or related to measurement.

7) To determine if there was local or systemic side effects or toxicity attributable to tile active ingredients or base.

8) To determine if multiple application resulted in equal, greater or reduced efficacy of any measurable or appearance of lip augmentation.

9) To determine if different bases affected tile efficacy of the various compounds.

PHYSIOLOGY AND PROPOSED MECHANISM OF ACTION

There are four erectile tissues in the body, namely the nipples, the penis/clitoris, the nose and both lips. Erection of the lip tissues is accomplished by increasing the blood volume of the lip blood vessels with blood by causing an arterial and arteriole and arteriolar vasodilatation with the blood flow into the lip exceeding blood flow out. We have previously noted three classes of pharmacologically active ingredients compounds result in one or both of these actions which in turn accomplishes an increased lip blood volume.

Compounds from three classes of active ingredients were used as representative in the studies:

1) Local lip irritant—Capsaicin, peppermint, ginger
2) Local lip vasodilator—Niacin, Korean Red Ginseng
3) Homeopathic dilutions of vasodilators, namely ultra high dilutions of elements, compounds.

OBJECTS AND ADVANTAGES OF THE INVENTION

The object of my invention is to provide a relatively simple method of lip augmentation that is widely affordable to those persons who desire to have an appearance of larger lips.

It is another object of the invention to provide a method of lip augmentation that is cosmetically appealing to the individual as well as to the perceiver.

A further object of the invention is to provide a method of lip augmentation that does not cause pain, complications, scarring, nor severe allergic reactions.

It is still another object of the invention to provide a method of lip augmentation that is not financially burdensome.

It is yet a further object of the invention to provide a method of lip augmentation that is quickly and conveniently changeable if the person does not like the appearance.

An additional object and advantage is to provide a method of lip augmentation that is widely available.

Still further objects and advantages will become apparent from a consideration of the ensuing description and accompanying tables.

PREFERRED EMBODIMENT—DESCRIPTION

DESCRIPTION OF MECHANISMS

The manner of using lip augmentation formula to cause lip augmentation is either by: applying the formula to either the vermilion surface of the lips with the fingertip or by lipstick; sublingually by drops or tablet or swishing through the mouth; or by chewing gum impregnated with the active ingredients of the particular formula utilized.

The active ingredients are divided into three individual groups or each element compound or group that results in lip augmentation may be combined with another active group of elements or compounds or combined with another active compound or element.

The topical base utilized can be any type of cream, gel or ointment that is capable of facilitating the absorption of the active ingredients into the submucosal layer of the lip.

The drops utilized contain 20% alcohol as a preservative with the remaining 80% containing water and one percent active ingredient.

The gum utilized is any standard gum with the active ingredients being impregnated in the gum or its coating.

The ultra-high dilution compounds and elements effect action based upon accepted homeopathic principles relating to molecular resonance and vibrations, thereby resulting in vasodilatation and consequently lip augmentation.

The topical vasodilators are local beta adrenergic receptor blocking agents or muscarinic acetylcholine receptor activators which result in a block of the norepinephrine receptors or cause a release of acetylcholine resulting in a dilatation of the blood vessels of the upper and lower lips.

The topical irritants result in a collection of metabolites in the lip region, lowering the regional pH and causing an increase in the regional pCO2 and thereby resulting in vasodilatation and lip erection.

STUDY

The cosmeceuticals developed for this study were based on the premise that there are four classes of erectile tissues in the body: the penis/clitoris; the nose; the nipples; and naturally the lips. Based upon the erectile capability of the lip, a new and unique combination of topical regional compounds were developed that resulted in achieving a lip "erection."

For five consecutive days, one different gel was applied by twenty women and four men ranging in age from fourteen to eighty years and of all body types. The ten "female active subjects" and two daily "male active subjects" applied with moderate pressure the active topical gel "lip augmenter" to the vermilion surface of both the upper and lower lips. Ten other "female placebo subjects" and two other "male placebo subjects" applied a placebo lip gel that was the same in all respects to the active gel except for the active ingredients. Each subject had a single application on five consecutive days consisting of five different gels, each on a separate day, in random order. The subjects also were randomly assigned to a placebo or active group on each particular day.

In the process of developing the various active lip ingredients, it was determined that different active ingredients were necessary in order to achieve augmentation of the upper versus the lower lip as well as the left versus the right sides of the same lip.

Although not reported in this study, the study observers noted that the female study subjects themselves subjectively self-rated the degree of their lip augmentation at between 20% to 100% larger. The average perceived maximum increase in lip augmentation of the study subjects was 39%, including three subjects who individually did not demonstrate a significant lip augmentation with any of the topical ingredients. These three subjects were determined to be impotent as far as lip erection was concerned.

Two of the study subjects had previously undergone lip enhancing collagen injections. Both of these subjects rated the results of this new topical method of lip augmentation superior and clearly far less painful than collagen injections.

Following the controlled study involving the topical active, four of the female subjects were tested utilizing sublingual drops, tablets and gum impregnated with Korea Red Ginseng, niacin and ultra high dilutions of Nux Vomica. Each of these ingredients resulted in perceivable and measurable lip augmentation which was significantly less than that observed by direct topical application.

CONCLUSIONS, RAMIFICATIONS AND SCOPE

Accordingly, it can be seen that I have provided a non-invasive method of cosmetic lip augmentation which is cosmetically appealing, convenient, pain-free, cost-effective, reversible and safe.

Although the description above contains many specificities, these should not be construed as limiting the scope of the invention but as merely providing illustrations of some of the presently preferred embodiments of this invention. Various other embodiments and ramifications are possible within its scope.

Thus the scope of the invention should be determined by the appended claims and their legal equivalents, rather than by the examples given.

APPENDIX A

STATISTICAL REPORT

COMPARATIVE COSMETIC LIP AUGMENTATION FOLLOWING TOPICAL

APPLICATION OF PLACEBO LIP GEL AND FOUR DIFFERENT

ACTIVE LIP GELS

COMPARATIVE COSMETIC LIP AUGMENTATION FOLLOWING TOPICAL

APPLICATION OF PLACEBO LIP GEL AND FOUR DIFFERENT

ACTIVE LIP GELS

Introduction

The purpose of this study was to evaluate and compare the safety and efficacy in the application of four active gels with combinations of active ingredients for the purpose of augmenting the size of the lips.

Materials and Methods

Twenty female and four male volunteer subjects were utilized in this study. All volunteers perceived their lips as being unattractively too thin, but were otherwise normal.

Five gels applied were as follows:

1. Placebo (with no active ingredient)
2. Gel containing ultra-highly diluted Elements (UHD)
3. Gel containing lip vasodilators
4. Gel containing mucous membrane irritants
5. Gel containing a combination of 2 and 3.

One gel was applied to both lips of each subject on a daily basis for five consecutive days. Each lip was measured with a cartographer's caliper prior to the application of the gel and then 5, 10, 15 minutes and 1, 2.5, 3, 4 and 5 hours after application. Baseline and post treatment measurements were measured from the line where the upper and lower lips meet in repose, to the apex of the cupid's bow on the right side of the upper lip; and from the line where the upper and lower lips meet in repose to the vermilion border in the midline of the lower lip. All measurements were recorded in millimeters. Both observers were asked to record their subjective impressions as well as measuring the lip size. Skin irritations, rashes and subjective sensations were also recorded.

The entire study was performed under double blind conditions in that neither the subject nor the observers knew which gel was placebo or which active.

Data Base

Appendices A1-1, A2-1 and B1-1 exhibit the maximum difference between lip measurements taken prior to and after application of gels. Appendices C1-1, C2-1 and D1-1 exhibit time to onset of lip augmentation. Appendices E1-1, E2-1 and F1-1 exhibit duration of augmentation. The values in these three sets of appendices constitute the basic data used in the analysis.

| | | | Results | | |
|---|---|---|---|---|---|
| GEL | MEAN | STD. ERR. | STD. DEV. | VAR- IANCE | p |
| 1. Analysis of Variance of Lip Augmentation Measurement in 20 Females | | | | | |
| PLACEBO | 0.050 | 0.087 | 0.552 | 0.305 | <0.0001 |
| UHD | 3.300 | 0.212 | 1.344 | 1.805 | <0.01 |
| VASODILAT | 2.125 | 0.187 | 1.181 | 1.394 | <0.01 |
| IRRITANT | 1.450 | 0.152 | 0.959 | 0.921 | <0.01 |
| COMBIN | 3.575 | 0.168 | 1.059 | 1.122 | <0.01 |
| 2. Analysis of Variance of Lip Augmentation Measurement in 4 Males | | | | | |
| PLACEBO | 0.000 | 0.000 | 0.000 | 0.000 | — |
| UHD | 0.000 | 0.189 | 0.535 | 0.286 | <0.001 |
| VASODILAT | 2.125 | 0.227 | 0.641 | 0.411 | <0.001 |
| IRRITANT | 1.125 | 0.227 | 0.641 | 0.411 | <0.001 |
| COMBIN | 2.125 | 0.227 | 0.641 | 0.411 | <0.001 |
| 3. Analysis of Variance of Time to Onset of Lip Augmentation in 20 Females | | | | | |
| UHD | 6.000 | 0.572 | 3.616 | 13.077 | >0.01 |
| VASODILAT | 9.625 | 1.258 | 7.957 | 63.317 | >0.001 |
| IRRITANT | 10.625 | 1.256 | 7.941 | 63.061 | >0.001 |
| COMBIN | 5.875 | 0.534 | 3.376 | 11.394 | >0.01 |
| 4. Analysis of Variance of Time to Onset of Lip Augmentation in 4 Males | | | | | |
| UHD | 20.625 | 2.903 | 8.210 | — | <0.0001 |
| VASODILAT | 8.125 | 0.915 | 2.588 | — | <0.0001 |
| IRRITANT | 9.375 | 2.577 | 7.289 | — | <0.0001 |
| COMBIN | 5.000 | 0.000 | 0.000 | — | <0.0001 |
| 5. Analysis of Variance of Duration of Lip Augmentation in 20 Females | | | | | |
| UHD | 4.425 | 0.208 | 1.318 | 1.738 | <0.01 |
| VASODILAT | 3.725 | 0.107 | 0.679 | 0.461 | <0.01 |
| IRRITANT | 2.825 | 0.285 | 1.631 | 2.661 | <0.001 |
| COMBIN | 5.025 | 0.131 | 0.832 | 0.692 | <0.01 |
| 6. Analysis of Variance of Duration of Lip Augmentation in 4 Males | | | | | |
| UHD | 0.875 | 0.581 | 1.642 | 2.696 | <0.0001 |
| VASODILAT | 3.625 | 0.263 | 0.744 | 0.554 | <0.001 |
| IRRITANT | 3.000 | 0.000 | 0.000 | 0.000 | <0.001 |
| COMBIN | 3.625 | 0.263 | 0.744 | 0.554 | <0.001 |

Analysis of female lip measurements demonstrated a highly significant linear trend for the lips treated with active gels containing UHD Elements or a combination of UHD Elements plus vasodilators toward a significant increase in lip size when compared to only vasodilators or local irritant active. The augmentation due to the UHD Elements or a combination of UHD Elements plus vasodilators were statistically highly significant (p<0.01). In males the same statistical significance was not observed (p<0.001).

Analysis of the speed with which these actives worked again showed highly statistically significance (p<0.01) in the females with the males once again responding poorly to the UHD plus combination (p<0.0001).

Analysis of significant augmentation in females demonstrated that the UHD and combination lasted an average of 4.425 hours and 5.025 hours respectively

Summary and Conclusions

Female subjects demonstrated significant upper and lower lip augmentation when topical gels containing either UHD Elements or a combination of UHD Elements plus vasodilators were applied. The onset of significant lip augmentation averaged close to five minutes. The duration of significant lip augmentation lasted greater than four hours.

Although the vasodilator gel and irritant gel individually increased lip size, the augmentation was generally less. Augmentation due to a combination of UHD Element plus vasodilator gel was the most pronounced. The vasodilator gel caused a mild transitory headache lasting less than five minutes in two females and one male. The irritant gel caused one male subject to experience a mild non-pruritic peri-oral rash that faded within 15 minutes without treatment.

Lip augmentation in males utilizing the four active combinations was not significant.

Newdata

|    | placebo | uhd   | vasodil | irritant | comb | lip | gender |
|----|---------|-------|---------|----------|------|-----|--------|
| 1  | .00     | 3.00  | 2.00    | 2.00     | 5.00 | u   | f      |
| 2  | −1.00   | 4.00  | 2.00    | 2.00     | 3.00 | l   | f      |
| 3  | .00     | 4.00  | 2.00    | 2.00     | 4.00 | u   | f      |
| 4  | −1.00   | 5.00  | 1.00    | 3.00     | 5.00 | l   | f      |
| 5  | 1.00    | 5.00  | 2.00    | 1.00     | 6.00 | u   | f      |
| 6  | .00     | 4.00  | 3.00    | 2.00     | 4.00 | l   | f      |
| 7  | .00     | 3.00  | 1.00    | .00      | 3.00 | u   | f      |
| 8  | .00     | 4.00  | 2.00    | .00      | 3.00 | l   | f      |
| 9  | 1.00    | 2.00  | 3.00    | 1.00     | 2.00 | u   | f      |
| 10 | .00     | 1.00  | 2.00    | .00      | 2.00 | l   | f      |
| 11 | .00     | 5.00  | 4.00    | 3.00     | 4.00 | u   | f      |
| 12 | 1.00    | 5.00  | 3.00    | 2.00     | 6.00 | l   | f      |
| 13 | .00     | .00   | .00     | 2.00     | 3.00 | u   | f      |
| 14 | .00     | 1.00  | −1.00   | 1.00     | 2.00 | l   | f      |
| 15 | .00     | 4.00  | 4.00    | 2.00     | 5.00 | u   | f      |
| 16 | .00     | 5.00  | 4.00    | 1.00     | 4.00 | l   | f      |
| 17 | 1.00    | 5.00  | 3.00    | 2.00     | 4.00 | u   | f      |
| 18 | .00     | 3.00  | 2.00    | 3.00     | 3.00 | l   | f      |
| 19 | .00     | 2.00  | 1.00    | .00      | 2.00 | u   | f      |
| 20 | .00     | 3.00  | 2.00    | 2.00     | 4.00 | l   | f      |
| 21 | .00     | 3.00  | 2.00    | 1.00     | 3.00 | u   | f      |
| 22 | .00     | 2.00  | 1.00    | 1.00     | 3.00 | l   | f      |
| 23 | −1.00   | 4.00  | 3.00    | 2.00     | 4.00 | u   | f      |
| 24 | .00     | 3.00  | 2.00    | 1.00     | 5.00 | l   | f      |
| 25 | 1.00    | 3.00  | 3.00    | 1.00     | 3.00 | u   | f      |
| 26 | 1.00    | 4.00  | 4.00    | 2.00     | 4.00 | l   | f      |
| 27 | .00     | 3.00  | 2.00    | .00      | 3.00 | u   | f      |
| 28 | .00     | 4.00  | 2.00    | .00      | 2.00 | l   | f      |
| 29 | .00     | 5.00  | 3.00    | 2.00     | 3.00 | u   | f      |

|    | placebo | uhd   | vasodil | irritant | comb | lip | gender |
|----|---------|-------|---------|----------|------|-----|--------|
| 30 | .00     | 4.00  | 4.00    | .00      | 2.00 | l   | f      |
| 31 | .00     | 4.00  | 2.00    | 2.00     | 3.00 | u   | f      |
| 32 | .00     | 5.00  | 2.00    | 2.00     | 4.00 | l   | f      |
| 33 | −1.00   | 1.00  | .00     | 2.00     | 4.00 | u   | f      |
| 34 | 1.00    | 2.00  | .00     | .00      | 3.00 | l   | f      |
| 35 | .00     | 3.00  | 3.00    | 1.00     | 5.00 | u   | f      |
| 36 | −1.00   | 3.00  | 2.00    | 1.00     | 4.00 | l   | f      |
| 37 | .00     | 4.00  | 1.00    | 3.00     | 3.00 | u   | f      |
| 38 | .00     | 4.00  | 2.00    | 3.00     | 4.00 | l   | f      |
| 39 | .00     | 2.00  | 2.00    | 2.00     | 3.00 | u   | f      |
| 40 | .00     | 1.00  | 3.00    | 1.00     | 4.00 | l   | f      |
| 41 | .       | .     | .       | .        | .    |     |        |
| 42 | .       | .     | .       | .        | .    |     |        |
| 43 | .       | .     | .       | .        | .    |     |        |
| 44 | .       | .     | .       | .        | .    |     |        |

|    | placebo | uhd   | vasodil | irritant | comb | lip | gender |
|----|---------|-------|---------|----------|------|-----|--------|
| 30 | .00     | 4.00  | 4.00    | .00      | 2.00 | l   | f      |
| 31 | .00     | 4.00  | 2.00    | 2.00     | 3.00 | u   | f      |
| 32 | .00     | 5.00  | 2.00    | 2.00     | 4.00 | l   | f      |
| 33 | −1.00   | 1.00  | .00     | 2.00     | 4.00 | u   | f      |
| 34 | 1.00    | 2.00  | .00     | .00      | 3.00 | l   | f      |
| 35 | .00     | 3.00  | 3.00    | 1.00     | 5.00 | u   | f      |
| 36 | −1.00   | 3.00  | 2.00    | 1.00     | 4.00 | l   | f      |
| 37 | .00     | 4.00  | 1.00    | 3.00     | 3.00 | u   | f      |
| 38 | .00     | 4.00  | 2.00    | 3.00     | 4.00 | l   | f      |
| 39 | .00     | 2.00  | 2.00    | 2.00     | 3.00 | u   | f      |

-continued

Newdata

|    |       |       |       |       |       |   |   |
|----|-------|-------|-------|-------|-------|---|---|
| 40 | .00   | 1.00  | 3.00  | 1.00  | 4.00  | l | f |
| 41 | .     | .     | .     | .     | .     |   |   |
| 42 | .     | .     | .     | .     | .     |   |   |
| 43 | .     | .     | .     | .     | .     |   |   |
| 44 | .     | .     | .     | .     | .     |   |   |

|   | uhd    | vasodila | irritant | comb  | lip |
|---|--------|----------|----------|-------|-----|
| 1 | 10.00  | 5.00     | 15.00    | 5.00  | u   |
| 2 | 25.00  | 10.00    | 10.00    | 5.00  | l   |
| 3 | 25.00  | 5.00     | 5.00     | 5.00  | u   |
| 4 | 25.00  | 10.00    | 5.00     | 5.00  | l   |
| 5 | 25.00  | 10.00    | 5.00     | 5.00  | u   |
| 6 | 5.00   | 10.00    | 25.00    | 5.00  | l   |
| 7 | 25.00  | 5.00     | 5.00     | 5.00  | u   |
| 8 | 25.00  | 10.00    | 5.00     | 5.00  | l   |

|    | uhd  | vasodila | irritant | comb | lip |
|----|------|----------|----------|------|-----|
| 1  | 5.00 | 4.00     | 3.00     | 6.00 | u   |
| 2  | 5.00 | 4.00     | 4.00     | 6.00 | l   |
| 3  | 5.00 | 3.00     | 4.00     | 6.00 | u   |
| 4  | 4.00 | 4.00     | 4.00     | 6.00 | l   |
| 5  | 4.00 | 4.00     | 4.00     | 6.00 | u   |
| 6  | 3.00 | 3.00     | 5.00     | 6.00 | l   |
| 7  | 3.00 | 4.00     | .00      | 5.00 | u   |
| 8  | 4.00 | 3.00     | .00      | 5.00 | l   |
| 9  | 5.00 | 4.00     | 3.00     | 3.00 | u   |
| 10 | 4.00 | 3.00     | .00      | 5.00 | l   |
| 11 | 5.00 | 3.00     | 3.00     | 5.00 | u   |
| 12 | 6.00 | 4.00     | 4.00     | 4.00 | l   |
| 13 | 3.00 | 3.00     | 3.00     | 4.00 | u   |
| 14 | 4.00 | 3.00     | 3.00     | 5.00 | l   |
| 15 | 3.00 | 3.00     | 4.00     | 5.00 | u   |
| 16 | 4.00 | 4.00     | 4.00     | 6.00 | l   |
| 17 | 5.00 | 4.00     | 3.00     | 6.00 | u   |
| 18 | 4.00 | 4.00     | 3.00     | 5.00 | l   |
| 19 | 3.00 | 3.00     | .00      | 4.00 | u   |
| 20 | 3.00 | 3.00     | 3.00     | 5.00 | l   |
| 21 | 3.00 | 3.00     | 3.00     | 5.00 | u   |
| 22 | 3.00 | 3.00     | 3.00     | 4.00 | l   |
| 23 | 4.00 | 4.00     | 4.00     | 5.00 | u   |
| 24 | 3.00 | 4.00     | 3.00     | 4.00 | l   |
| 25 | 4.00 | 4.00     | 3.00     | 5.00 | u   |
| 26 | 5.00 | 4.00     | 4.00     | 6.00 | l   |
| 27 | 6.00 | 4.00     | .00      | 5.00 | u   |
| 28 | 5.00 | 3.00     | .00      | 6.00 | l   |
| 29 | 6.00 | 6.00     | 4.00     | 4.00 | u   |

|    | uhd  | vasodila | irritant | comb | lip |
|----|------|----------|----------|------|-----|
| 30 | 5.00 | 5.00     | .00      | 4.00 | l   |
| 31 | 5.00 | 4.00     | .00      | 5.00 | u   |
| 32 | 5.00 | 4.00     | 4.00     | 5.00 | l   |
| 33 | 3.00 | 3.00     | 3.00     | 4.00 | u   |
| 34 | 4.00 | 3.00     | .00      | 4.00 | l   |
| 35 | 5.00 | 5.00     | 4.00     | 6.00 | u   |
| 36 | 4.00 | 4.00     | 4.00     | 5.00 | l   |
| 37 | 4.00 | 4.00     | 4.00     | 4.00 | u   |
| 38 | 4.00 | 4.00     | 4.00     | 6.00 | l   |
| 39 | 8.00 | 4.00     | 5.00     | 6.00 | u   |
| 40 | 9.00 | 4.00     | 4.00     | 5.00 | l   |
| 41 | .    | .        | .        | .    |     |
| 42 | .    | .        | .        | .    |     |
| 43 | .    | .        | .        | .    |     |

|   | uhd  | vasodila | irritant | comb | lip |
|---|------|----------|----------|------|-----|
| 1 | 4.00 | 3.00     | 3.00     | 3.00 | u   |
| 2 | 3.00 | 3.00     | 3.00     | 3.00 | l   |
| 3 | .00  | 5.00     | 3.00     | 5.00 | u   |
| 4 | .00  | 4.00     | 3.00     | 4.00 | l   |
| 5 | .00  | 3.00     | 3.00     | 3.00 | u   |
| 6 | .00  | 4.00     | 3.00     | 4.00 | l   |
| 7 | .00  | 4.00     | 3.00     | 4.00 | u   |
| 8 | .00  | 3.00     | 3.00     | 3.00 | l   |

SUMMARY OF RESULTS

OBJECTIVE:
Average increase in size of lips (mm)

| Treatment: | Females: | | | Males: | | |
| --- | --- | --- | --- | --- | --- | --- |
| | U* | L | Ave. | U | L | Ave. |
| 1. UHD Elements | 3.25 | 3.35 | 3.30 | 0.25 | 0.25 | 0.25 |
| 2. Vasodilators | 2.15 | 2.10 | 2.13 | 2.25 | 2.00 | 2.13 |
| 3. Irritants | 1.55 | 1.35 | 1.45 | 1.00 | 1.25 | 1.13 |
| 4. Combination 1 + 2 | 3.60 | 3.55 | 3.58 | 2.50 | 1.75 | 2.13 |

*U - Upper Lip   L - Lower Lip   Ave. - Mean Average of Upper and Lower Lips

SUBJECTIVE:

Females: Numbers represent increase observed in size of lip - total of 40 lips.

| Treatment | Observer #1 | Observer #2 |
| --- | --- | --- |
| 1. UHD Elements | 31 of which 4 were considered greatly enlarged | 32 of which 16 were considered greatly enlarged |
| 2. Vasodilators | 22 of which 3 were considered greatly enlarged | 26 of which 4 were considered greatly enlarged |
| 3. Irritants | 14 of which 0 were considered greatly enlarged | 11 of which 1 was considered greatly enlarged |
| 4. Combination 1 + 2 | 36 of which 9 were considered greatly enlarged | 39 of which 16 were considered greatly enlarged |

Males: Numbers represent increase observed in size of lip - total of 8 lips.

| Treatment | Observer #1 | Observer #2 |
| --- | --- | --- |
| 1. UHD Elements | 0 of which 0 were considered greatly enlarged | 1 of which 0 were considered greatly enlarged |
| 2. Vasodilators | 5 of which 0 were considered greatly enlarged | 6 of which 1 was considered greatly enlarged |
| 3. Irritants | 1 of which 0 were considered greatly enlarged | 3 of which 0 were considered greatly enlarged |
| 4. Combination 1 + 2 | 5 of which 0 were considered greatly enlarged | 6 of which 1 was considered greatly enlarged |

TIME TO ONSET OF ENLARGEMENT:

Females: 40 lips measured at 5, 10 and 15 minutes after applying treatment.

| Treatment | 5 Minutes | 10 Minutes | 15 Minutes |
| --- | --- | --- | --- |
| 1. UHD Elements | 35 | 3 | 1 |
| 2. Vasodilators | 27 | 5 | 0 |
| 3. Irritants | 23 | 5 | 4 |
| 4. Combination 1 + 2 | 36 | 3 | 0 |

Males: 8 lips measured at 5, 10 and 15 minutes after applying treatment.

| Treatment | 5 Minutes | 10 Minutes | 15 Minutes |
| --- | --- | --- | --- |
| 1. UHD Elements | 2 | 0 | 0 |
| 2. Vasodilators | 3 | 5 | 0 |
| 3. Irritants | 5 | 1 | 1 |
| 4. Combination 1 + 2 | 4 | 4 | 0 |

DURATION OF ENLARGEMENT:

Females: 40 lips measured at 3, 4 and 5 hours after applying treatment.

| Treatment | 3 Hours | 4 Hours | 5 Hours | >5 Hours |
| --- | --- | --- | --- | --- |
| 1. UHD Elements | 11 | 14 | 12 | 3 |
| 2. Vasodilators | 15 | 22 | 2 | 1 |
| 3. Irritants | 13 | 16 | 3 | 0 |
| 4. Combination 1 + 2 | 1 | 10 | 16 | 1 |

Males: 8 lips measured at 3, 4 and 5 hours after applying treatment.

| Treatment | 3 Hours | 4 Hours | 5 Hours | >5 Hours |
| --- | --- | --- | --- | --- |
| 1. UHD Elements | 1 | 1 | 0 | 0 |
| 2. Vasodilators | 4 | 3 | 1 | 0 |
| 3. Irritants | 8 | 0 | 0 | 0 |
| 4. Combination 1 + 2 | 4 | 3 | 1 | 0 |

OVERALL SUMMARY OF RESULTS (FEMALES)

1. Range of onset of tingling of one or both lips — 1 to 12 minutes.
2. Range of maximum increase (or decrease) of upper lip — 0 to +6 mm.
3. Range of maximum increase (or decrease) of lower lip — −1 to +6 mm.
4. Average duration of significant augmentation of upper and lower lips — 3.8 hours.
5. Most effective active formula — Combination of UHD and Vasodilators.
6. Least effective active formula — Irritants.

APPENDIX B

LIST OF INGREDIENTS IN COSMETIC LIP AUGMENTATION GELS

LIP GEL A (UHD):
Fancorsil—HA—Super
Aloe Vera
Rice Bran Oil
Carbomer 940
Phenonip
Uniphen
Lecinol
Silhydrate "C"
Hydroxyprolisilane "C"
Adenosine 6X
Nux Vomica 6X
Phosphorus 6X
Yttrium 6X LIP GEL B (Vasodilator):
Fancorsil—HA—Super
Aloe Vera
Rice Bran Oil
Carbomer 940
Phenonip
Uniphen
Lecinol
Silhydrate "C"
Hydroxyprolisilane "C"
Niacin
Korean Red Ginseng LIP GEL C (Irritant):
Fancorsil—HA—Super
Aloe Vera
Rice Bran Oil
Carbomer 940
Phenonip
Uniphen
Lecinol
Silhydrate "C"
Hydroxyprolisilane "C"
Ginger Extract
Peppermint Extract
Extract of Cloves LIP GEL D (Combination of Gels A & B):
Fancorsil—HA—Super
Aloe Vera
Rice Bran Oil
Carbomer 940
Phenonip
Uniphen
Lecinol
Silhydrate "C"
Hydroxyprolisilane "C"
Adenosine 6X
Nux Vomica 6X
Phosphorus 6X
Yttrium 6X
Niacin
Korean Red Ginseng

APPENDIX C

METHOD OF PREPARATION OF COSMETIC LIP AUGMENTATION GELS

Introduction

Five different categories of active gels were used to achieve the appearance of cosmetic lip augmentation. These five categories were classified according to the active ingredients. The active ingredients were divided as follows;

1. A mixture of Ultra High Dilutions (UHD) of certain elements.
2. Local direct vasodilators.
3. Local irritants.
4. Biologically natural homeopathics.
5. A combination of categories 1 and 2 or 1,2 and 3, or 1 and 3, or 2 and 3.

The standard cosmetic cream or gel base used is common to all five categories.

Example of Dosage

A single dose of each cosmetic gel is applied with moderate pressure to the vermilion of the upper and lower lips. The amount of gel applied is directed to be that amount of gel contained on the tip of the fifth finger.

STEP ONE

Preparation of Base

Any standard cosmetic gel or standard cosmetic cream base will be sufficient. An example of the formulation of the gel base consists of the following ingredients with their given percentages.

| | |
|---|---|
| Fancorsil - HA - Super | 45% |
| Aloe Vera | 20% |
| Water | 15% |
| Rice Bran Oil | 10% |
| Carbomer 940 | 4% |
| Lecinol | 2% |
| Phenonip | 1% |
| Uniphen | 1% |
| Silhydrate "C" | 1% |
| Hydroxyprolisilane "C" | 1% |

The above ingredients were mixed together, in a clean but not necessarily sterile mixing container, at room temperature except for the Carbomer 940 which was dissolved in boiling water before adding it to the remainder of the mixture. The resulting compounded mixture was then stirred into a smooth gel before the active ingredients were added.

STEP 2—ACTIVE INGREDIENTS

Example of Preparation of UHD Elements as Active Ingredients IN Topical Gel:

The following were mixed together in equal proportions;
Adenosine 6X
Phosphorus 6X
Yttrium 12X
Gold 1M These preparations were purchased from New Vista Homeopathic Company in Denver, Colo. They contained a diluent of water (80%) and ethanol (20%). This mixture was added to the base as 15% of the total volume. This was performed at room temperature.

Example of Preparation of Vasodilators as Active Ingredients

The following were mixed together in equal proportions;
Niacin (Vitamin B3)
Korean Red Ginseng Although the Ginseng really acts as a lipogenetic agent, for this purpose it appears to act synergistically with Niacin in producing the desired effect. Both Ginseng and Niacin are dissolved in boiling water and stirred well. When their temperature decreases to 82° C. the mixture is added to the base, in the concentration of 10% of the total, and stirred well until the gel settles.

Example of Preparation of Irritants as Active Ingredients

The following were mixed together at room temperature and in equal proportions;
Ginger Extract
Peppermint Extract
Extract of Cloves After mixing well these ingredients were added to the base as 10% of the total.

Example of Preparation of a combination of UHD Elements+Vasodilators as Active Ingredients The percentage of each ingredient need not be exact. Preparation of the formula should include these active ingredients in approximately equal proportions. The following were prepared as discussed in their respective sections and mixed together;
Adenosine 6X
Phosphorus 6X
Yttrium 12X
Gold 1M
Niacin
Korean Red Ginseng This mixture was added to the base as 15% of the total.

Ingredients

UHD Elements:
Adenosine 1M
Phosphorus 1M
Yttrium 1M
Gold 1M
Phosphorus 1M
Zinc 1M
Strontium 1M
Nickel 1M
Titanium 1M
Nitrogen 1M
  Vasodilators:
Niacin
Nicotinic Acid
Korean Red Ginseng
Resorcinol
Acetylcholine
Pyro-Glutamic Acid
  Irritants:
Ginger Extract
Peppermint Extract
Extract of Cloves
Croton Oil
  Herbs and Homeopathics:
Nux Vomica 6X
Cimicifuga Rac. 3X
Histamine 200X
Picricum Acidum 60C
Viscum Album 5X
Sanguianaria Nitricum 6X

I claim:

1. A process for achieving a selective augmentation of the size of the upper and lower lips comprising delivery specifically to the lips where the augmentation is sought, an effective amount of vasodilator.

2. The process of claim 1 wherein said delivery step to the lips in achieved by topical application of the vasodilator in a cosmetic base to the surface of the lips.

3. The process of claim 1 wherein said delivery step is achieved by sublingual administration of a tablet or drops.

4. The process of claim 1 wherein said delivery step is achieved by administration of chewing gum.

5. The process of claim 1 wherein said vasodilator is selected from the direct vasodilator group consisting of niacin, Korean Red Ginseng, acetylcholine, resorcinol and pyroglutamic acid.

6. The process of claim 5 wherein said delivery step is achieved by topical application.

7. The process of claim 1 wherein the vasodilator is selected from an ultra high dilution of elements specifically phosphorous 1M and yttrium 1M and/or one or more homeopathic compounds, specifically nux vomica, niacin and capsicum.

8. The process of claim 7 wherein said delivery step is achieved by topical application.

9. The process of claim 7 wherein said delivery step is achieved by sublingual administration of drops or a tablet.

10. The process of claim 7 wherein the delivery step is achieved by chewing gum impregnated with active ingredients.

11. The process of claim 1 wherein the vasodilator is selected from a local irritant group of compounds consisting of capsicum, peppermint, ginger extract and/or cloves.

12. The process of claim 1 wherein the vasodilator is a combination of individual components referred to in claims 5, 7 or 11.

* * * * *